United States Patent
Zhang et al.

(10) Patent No.: US 8,792,089 B2
(45) Date of Patent: Jul. 29, 2014

(54) DEVICE FOR DETERMINING A CONCENTRATION OF A CONSTITUENT OF BLOOD IN A HOSE LINE

(75) Inventors: Wei Zhang, Niederwerrn (DE); Elke Schulte, Schweinfurt (DE); Martin Kaiser, Hassfurt (DE); Carsten Mueller, Euerbach (DE); Tom Klein, Schweinfurt (DE); Stefan Zerle, Coburg (DE); Christoph Bardorz, Rottendorf (DE); Stefan Stuehler, Schonungen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 82 days.

(21) Appl. No.: 13/554,145

(22) Filed: Jul. 20, 2012

(65) Prior Publication Data

US 2013/0033697 A1 Feb. 7, 2013

Related U.S. Application Data

(60) Provisional application No. 61/510,104, filed on Jul. 21, 2011.

(30) Foreign Application Priority Data

Jul. 21, 2011 (DE) .......................... 10 2011 108 050

(51) Int. Cl.
*G01N 33/48* (2006.01)
(52) U.S. Cl.
USPC .......................................................... 356/39
(58) Field of Classification Search
USPC .......................................... 356/39; 600/322
See application file for complete search history.

(56) References Cited

U.S. PATENT DOCUMENTS 3,711,708 A * 1/1973 Dolin et al. .................... 250/343
3,972,614 A * 8/1976 Johansen et al. ................ 356/36

(Continued)

FOREIGN PATENT DOCUMENTS

DE 19530969 A1 2/1997
DE 29713696 U1 9/1997

(Continued)

OTHER PUBLICATIONS

PCT International Search Report from PCT/EP2012/003087, mailed Apr. 24, 2013.

*Primary Examiner* — Roy M Punnoose
(74) *Attorney, Agent, or Firm* — Kenyon and Kenyon LLP

(57) ABSTRACT

A device for determining the concentration of a constituent of blood in a hose line, in particular in the hose line of an extracorporeal blood circuit of an extracorporeal blood treatment apparatus, includes a clamping unit having an actuation mechanism configured to apply a clamping force such that first and second receiving elements are moved towards one another from a first position releasing the hose line into a second position clamping the hose line, in which the drive of the actuation mechanism takes place with an electric motor, and a monitoring unit configured to detect a hose line inserted into the receiving elements. A method for detecting a hose line in a clamping unit of a device for determining the concentration of a blood constituent in the hose line is also described. Automation of the measurement of the blood parameters is thus possible.

17 Claims, 11 Drawing Sheets

(56) References Cited

U.S. PATENT DOCUMENTS

| | | | |
|---|---|---|---|
| 4,902,132 A * | 2/1990 | Murphy et al. | 356/339 |
| 5,009,503 A * | 4/1991 | Murphy et al. | 356/339 |
| 5,372,136 A | 12/1994 | Steuer et al. | |
| 6,174,447 B1 | 1/2001 | Spindler | |
| 2011/0063607 A1 * | 3/2011 | Maurer et al. | 356/244 |

FOREIGN PATENT DOCUMENTS

| | | |
|---|---|---|
| DE | 69412898 T2 | 3/1999 |
| DE | 102009005402 A1 | 7/2010 |
| WO | 2004/057313 A1 | 7/2004 |
| WO | 2008/000433 A1 | 1/2008 |

* cited by examiner

|  | A (Min ~ Max) [ mA * Strecke ] | | max. I (Min ~ Max) [ mA ] | | dI / dx | |
| --- | --- | --- | --- | --- | --- | --- |
|  | PVC | PUR | PVC | PUR | PVC | PUR |
| Fig. 8A | 133,9 ~ 226,8 | 590,8 ~ 1001,9 | 10,2 ~ 12,4 | 19,2 ~ 25,3 | 0,122 ~ 0,137 | 0,225 ~ 0,334 |
| Fig. 8B | 256,1 ~ 388 | 784,0 ~ 1612,2 | 13,2 ~ 15,0 | 23,1 ~ 28,5 | 0,185 ~ 0,192 | 0,337 ~ 0,355 |
| Fig. 8C | 283,1 ~ 303,3 | 859,0 ~ 1167,5 | 13,5 ~ 14,2 | 24,7 ~ 29,7 | 0,187 ~ 0,210 | 0,341 ~ 0,366 |
| Fig. 8D | 399,7 ~ 483,5 | 977,2 ~ 1422,5 | 15,9 ~ 17,0 | 26,2 ~ 32,9 | 0,166 ~ 0,172 | 0,329 ~ 0,355 |
|  | 133,9 ~ 483,5 | 590,8 ~ 1612,2 | 10,2 ~ 17,0 | 19,2 ~ 32,9 | 0,122 ~ 0,210 | 0,225 ~ 0,366 |
|  | Δ = 107,3 20% von (483,5 + 590,8)/2 | | Δ = 2,2 12% von (17,0 + 19,2)/2 | | Δ = 0,015 7% von (0,210 + 0,225)/2 | |

Fig. 9

DEVICE FOR DETERMINING A CONCENTRATION OF A CONSTITUENT OF BLOOD IN A HOSE LINE

CROSS-REFERENCES TO RELATED APPLICATIONS

The present application claims priority to U.S. Provisional Application No. 61/510,104, filed on Jul. 21, 2011, and claims priority to Application No. DE 10 2011 108 050.7, filed in the Federal Republic of Germany on Jul. 21, 2011, each of which is expressly incorporated herein in its entirety by reference thereto.

FIELD OF INVENTION

The present invention relates to a device for determining the concentration of a constituent of blood in a hose line, in particular in the hose line of an extracorporeal blood circuit of an extracorporeal blood treatment apparatus. Moreover, the present invention relates to a method for detecting a hose line, in particular a hose line of an extracorporeal blood circuit of an extracorporeal treatment apparatus, in a clamping unit of a device for determining the concentration of a blood constituent in the hose line.

BACKGROUND INFORMATION

Various methods are known for determining the concentration of specific constituents of a patient's blood. Methods for measuring the concentration of blood constituents which require a blood sample to be taken are known in the prior art. Measurement methods are however also known, in which the concentration of blood constituents is measured while the blood is flowing through the hose line. These methods are used especially when the blood is flowing through the hose line of an extracorporeal blood circuit in an extracorporeal blood treatment.

International Patent Publication No. WO 2008/00433 describes a device for determining the concentration of specific blood constituents in a blood-filled, essentially transparent hose line of an extracorporeal blood circuit. The known device makes it possible in particular to determine the haemoglobin concentration and the fraction of red blood corpuscles (erythrocytes) in the total volume of the blood. During the measurement, the hose line is clamped between two parallel, plane contact surfaces, so that the hose is deformed at the sides lying opposite one another. With a light emitter, light of a specific wavelength is coupled through the transparent hose line into the blood, whilst the scattered or transmitted light is measured with a light detector. The haematocrit is then determined from the ratio of the intensity of the light entering into the blood and emerging from the blood.

There is known from European Patent No. EP 1 579 196 a device for determining blood constituents, which comprises a clamping unit for clamping the hose line and a measurement unit. The clamping unit is constituted such that the clamped hose line has a square cross-section. The measurement unit comprises a plurality of light emitters and light detectors which are disposed around the periphery of the hose line. The light emitters and light detectors are disposed in such a way that the light emitters lie in a different plane from the light detectors, so that light emitters and light detectors do not lie opposite one another. For the measurement of the blood parameters, the hose line is deformed in the clamping unit. It must be ensured that the hose line does not get jammed in the clamping unit.

Moreover, it is sought to make reproducible measurements of the blood parameters possible for the user without great expense. Automation of the measurement sequence also requires the detection of the hose lines inserted into the clamping unit. The power and the service life of the light-emitting diodes (LEDs) used as light emitters also play a role in the measurement in practice.

SUMMARY

A problem addressed by the present invention is to provide a device for determining the concentration of blood parameters in a hose line, which permits an automated measurement sequence with a high measurement accuracy.

A further problem addressed by the present invention is to provide a method for detecting a hose line in a clamping unit of a device for determining the concentration of a blood constituent.

The device according to the present invention for determining the concentration of a constituent of blood in a hose line, in particular the hose line of an extracorporeal blood circuit, is characterised in that the clamping unit comprises an actuation mechanism, which is constituted such that, when a clamping force is applied, a first and second receiving element can be moved towards one another from a first position releasing the hose line into a second position clamping the hose line, in which the drive of the actuation mechanism takes place with an electric motor. A fully automatically operating clamping unit is thus created, into which the user merely has to insert the hose line.

Since the two receiving elements for the hose line are moved towards one another by means of an electric motor, the required clamping force is applied uniformly. The electric-motor drive permits the adjustment of a specific feed rate at which the receiving elements are moved. It is thus possible to compress the hose line at an optimum feed rate, so that the hose line has the opportunity to centre itself exactly between the receiving elements. Jamming of the hose line due to an excessively rapid and non-uniform movement of the clamping elements is thus avoided.

Moreover, the device according to the present invention for determining the concentration of blood constituents is characterised by a monitoring unit, which is constituted such that the hose line inserted into the receiving elements can be detected. Automation of the measurement of the blood parameters is thus possible. For example, the measurement can be started not until and only when the hose line is inserted into the clamping unit. The light-emission period of the LEDs used as light emitters can thus be reduced, so that the service life of the LEDs is increased. Moreover, incorrect measurements are avoided when the hose line is not inserted.

In a preferred embodiment, the motor current of the electric motor for driving the actuation mechanism of the clamping unit is measured in order to detect the hose line in the clamping unit, in which the hose line inserted into the receiving elements of the clamping unit is detected on the basis of the change in the measured motor current. Instead of the motor current of the electric motor for driving the actuation mechanism, any variable correlating with the motor current, for example the motor power, can also be evaluated. The evaluation of the motor current for detecting the hose line can take place in a computing and evaluation unit, without other mechanical components being required. The computing and evaluation unit of the monitoring device can be a component part of the computing and evaluation unit of the device for determining the concentration of the blood constituent. Both computing and evaluation units can also be a component part of the central control unit or computing and evaluation unit of an extracorporeal blood treatment apparatus.

It has been shown that the motor current has a characteristic course, which is dependent on whether a hose line is clamped or not. When the receiving elements close, a marked increase in the motor current appears much earlier when the hose line is inserted into the receiving elements. The increase in the motor current is also much steeper when the hose line is inserted. The time-related course of the motor current during the closing of the receiving elements can thus be used as a criterion for the detection of the hose line.

In a particularly preferred embodiment, the monitoring unit comprises a unit for measuring the path covered by the receiving elements, in which the computing and evaluation unit of the monitoring unit is constituted such that the motor current is evaluated as a function of the path covered by the receiving elements. In the particularly preferred embodiment, the computing and evaluation unit is constituted such that the integral of the motor current over a preset path covered by the receiving elements is compared with a preset threshold value, it being concluded that, when the threshold value is exceeded, a hose line is inserted into the receiving elements. The integration of the motor current does not need to take place continuously, but can also take place in discrete time intervals. The threshold value can be preset as a function of the material of the hose line used, a plurality of threshold values also being able to be preset for different hose lines.

A particularly preferred embodiment of the clamping unit, which has its own inventive significance, is characterised in that the first receiving element comprises two plane contact faces standing at right angles to one another and the second receiving element comprises two plane contact faces standing at right angles to one another, in which the first and second receiving elements can be moved towards one another on an axis which forms an angle of 45° with the plane contact faces of the first and second receiving elements. It is unimportant here how the two receiving elements are constituted, as long as the plane contact faces standing at right angles to one another are present.

The receiving elements with the plane contact faces deform the hose line when the clamping unit is closed. The first and second receiving elements preferably comprise semi-cylindrical contact faces on both sides of the plane contact faces. The inserted hose line is not deformed in the region of the semi-cylindrical contact faces.

A particularly preferred embodiment provides a transition section between the plane contact faces and the semi-cylindrical contact faces of the two receiving elements, said transition section being constituted such that the inner plane contact faces are transformed continuously into the outer semi-cylindrical contact faces. A continuous transition is understood to mean any transition which permits a uniform deformation of the hose line, so that the circular cross-section of the hose line is transformed uniformly into the square cross-section and the hose line is not kinked.

The uniform transition from the circular to the square cross-section not only has the advantage that the hose line is protected when the clamping unit is closed, but also the advantage that turbulent currents are avoided during the transition from the round to the square line cross-section. The length of the square measuring channel, in which light emitters and light detectors are disposed, can thus be kept as small as possible. Shortening of the measuring channel in turn leads to small closing forces, which is also advantageous.

The measurement unit of the device for determining the concentration of blood constituents preferably comprises a plurality of light emitters for the coupling of electromagnetic radiation through the hose line into the blood and a plurality of light detectors for measuring the electromagnetic radiation emerging through the hose line from the blood, which are disposed in the first and second receiving element. The light emitters and the light detectors are preferably disposed in light outlet and light inlet openings, which are provided in the plane contact faces of the receiving elements. The light emitters and light detectors are thus integrated into the receiving elements.

In a preferred embodiment of the measurement unit, which has its own inventive significance, at least one group of two light emitters is assigned to at least one light detector. For example, 2, 4, 6 or 8 light emitters can be assigned to the at least one light detector. In practice, however, the assignment of 2 light emitters to a light detector is sufficient.

The use of two light emitters instead of only one light emitter for coupling light into the hose line has the advantage that the light yield of the LEDs is doubled, whereas the influence of the hose line on the distance covered by the light is reduced.

It is a drawback that the signal amplitude diminishes with an increasing distance between light emitter and light detector. In principle, therefore, an increase in the intensity of the coupled light is sought. This however considerably limits the selection of the components available as light emitters. A smaller distance between light emitters and light detectors, which does not necessitate an increase in the intensity of the radiation, on the other hand has an adverse effect on the accuracy of the measurement. In addition, there are variations in the hose wall thickness, which cannot be ruled out on short sections of the hose lines with the known extrusion processes for the production of hose lines. The hose therefore has the same wall thickness over its whole extent only to a first approximation.

The combination of two light emitters disposed on opposite sides of the hose line to form a group doubles the light yield. Since the light of the two light emitters is evaluated on different measurement sections, the influences of the hose line are averaged out, as a result of which the measurement accuracy is increased.

The special embodiment of the receiving elements of the clamping unit with the plane and cylindrical contact faces does not necessarily require a special embodiment of the measurement unit and a special embodiment of the clamping unit with the actuation mechanism, which comprises an electric-motor drive. The special embodiment of the measurement unit likewise does not require a special embodiment of the receiving elements of the clamping unit and a special embodiment of the electric motor-driven actuation mechanism of the clamping unit.

An exemplary embodiment of the present invention is explained below in greater detail with reference to the accompanying drawings.

BRIEF DESCRIPTION OF THE DRAWINGS

FIG. 9 shows a table in which the integral, the maximum current and the edge gradient of the current increase for the clamping units of the same design and the different hose types are entered, according to an exemplary embodiment of the present invention.

DETAILED DESCRIPTION

Figure 1:
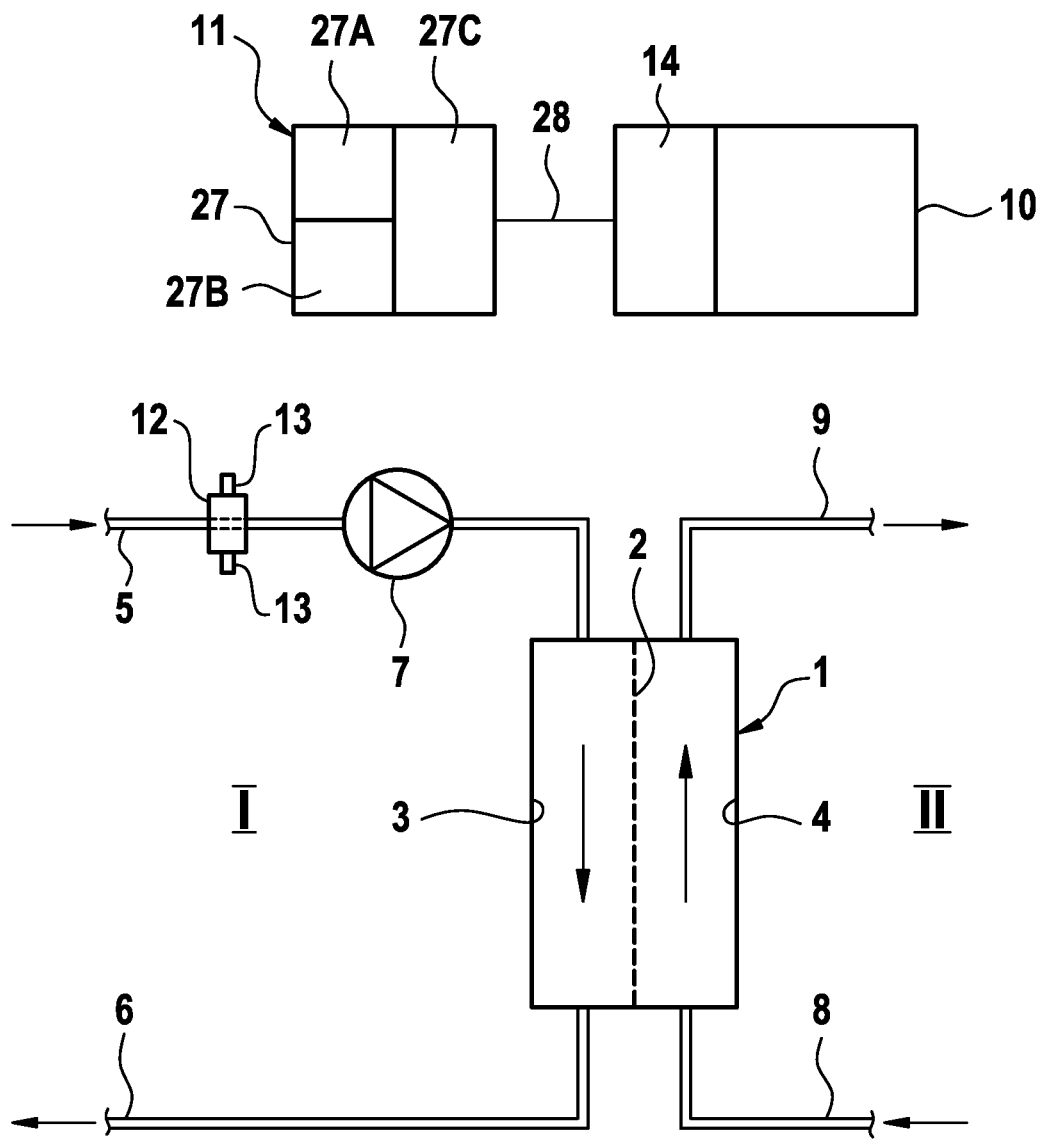
FIG. 1 shows an apparatus for extracorporeal blood treatment together with a device for determining the concentration of a blood constituent in a very simplified schematic representation according to an exemplary embodiment of the present invention.

FIG. 1 shows only the components of an apparatus for extracorporeal blood treatment that are essential to the present invention, in a very simplified diagrammatic representation. The extracorporeal blood treatment apparatus, for example a dialysis apparatus, comprises a dialyser or filter 1, which is divided by a semipermeable membrane 2 into a blood chamber 3 and a dialysing fluid chamber 4. An arterial blood line 5 leads from the patient to blood chamber 3, whilst a venous blood line 6 leads away from the blood chamber 3 and to the patient. A blood pump 7 disposed in arterial blood line 5 conveys the blood in extracorporeal blood circuit I. Dialysing fluid system II of the dialysis apparatus is represented only in outline. It comprises a dialysing fluid supply line 8 leading to dialysing fluid chamber 4 and a dialysing fluid discharge line 9 leading away from dialysing fluid chamber 4. Arterial and venous blood lines 5, 6 are hose lines which are at least partially permeable to light. Furthermore, the blood treatment apparatus comprises a central control unit 10, with which the individual components, for example blood pump 7, are controlled.

Device 11 for determining the concentration of specific blood constituents in a patient's blood can be a component part of the extracorporeal blood treatment apparatus or form a separate component. When device 11 is a component part of the blood treatment apparatus, it can make use of components which are in any case present in the blood treatment apparatus.

Device 11 for determining the concentration of blood Constituents, in particular the haemoglobin concentration (Hb), the haematocrit (Hkt) or the relative blood volume (RBV), comprises a clamping unit 12, represented only in outline in FIG. 1, for receiving the hose line, in particular arterial blood line 5, and a measurement unit 13 for coupling light into the blood flowing through blood line 5 and measuring the light emerging from the blood. Measurement unit 13 cooperates with a computing and evaluation unit 14, which determines the concentration of the blood constituent from the measured values. The description of the evaluation of the measured values for determining the blood constituents in detail will be dispensed with, since the determination of the concentration of the blood constituent from the measured values is known. The determination of the blood constituents is described in detail for example in European Patent No. EP 1 579 196.

In the present exemplary embodiment, computing and evaluation unit 14 for determining the concentration of a blood constituent is a component part of central control unit 10 or the computing and evaluation unit of the extracorporeal blood treatment apparatus. Separate units can however also be provided.

Figure 2A:
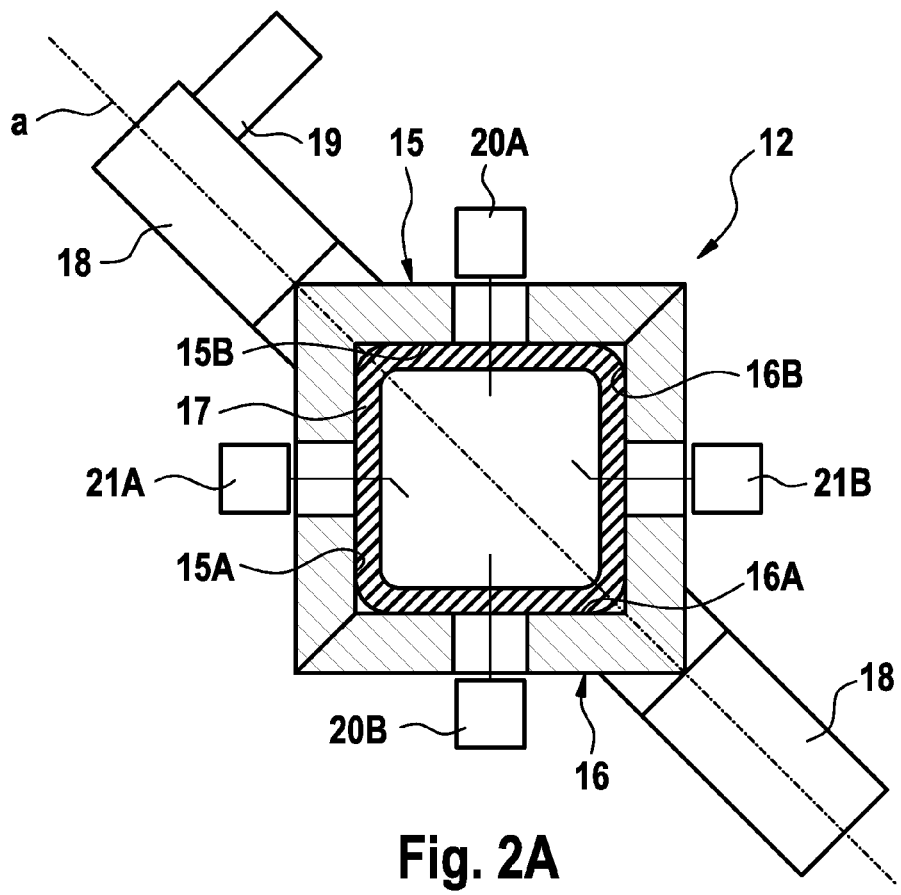
FIG. 2A shows a very simplified schematic representation of the clamping unit and the measurement unit of the device for determining the concentration of a blood constituent, in which the arrangement of the light emitters and the light detectors is shown in a first cross-sectional plane, according to an exemplary embodiment of the present invention.
Figure 2B:
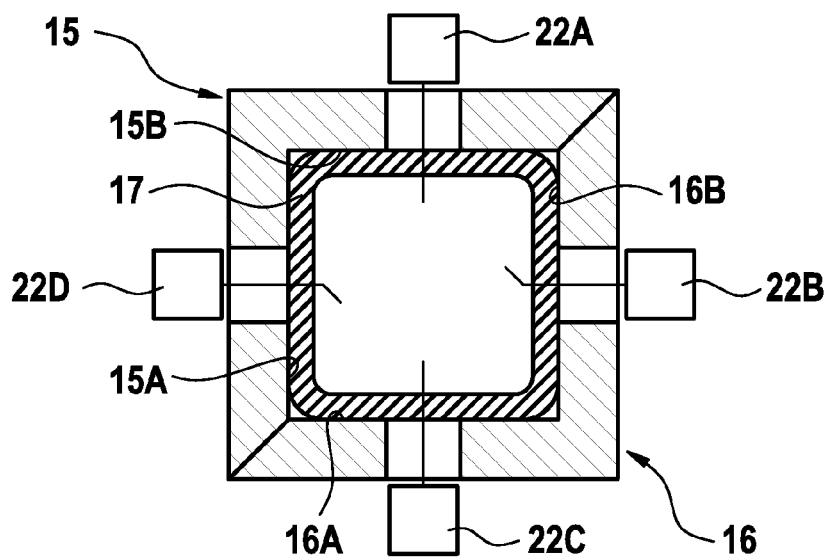
FIG. 2B shows the clamping unit and the measurement unit in a very simplified schematic representation, in which the arrangement of the light emitters and light detectors is shown in a second cross-sectional plane, which is different from the first cross-sectional plane, according to an exemplary embodiment of the present invention.

FIGS. 2A and 2B show, in different cross-sectional planes and in a very simplified schematic representation, clamping unit 12 and measurement unit 13 of device 11.

Clamping unit 12 comprises two receiving elements 15, 16, between which hose line 17 is clamped, so that the round hose line acquires a square cross-section. For the insertion of the hose line, receiving elements 15, 16 can be moved towards one another along an axis a. An actuation mechanism 18, which is represented only schematically in FIGS. 2A and 2B, is used to move clamping elements 15, 16 from a position releasing hose line 17 into a position clamping the hose line.

Receiving elements 15, 16 and actuation mechanism 18 can be constituted differently. An electric motor 19, which is also represented only schematically, is used to drive actuation mechanism 18. When the electric motor rotates in the one or other direction, the receiving elements are opened and closed along axis a. FIGS. 2A and 2B show clamping unit 12 in the closed position.

Receiving elements 15, 16 each comprise two plane contact faces 15A, 15B and 16A, 16B respectively, which in each case form a right angle. Axis a, on which receiving elements 15, 16 are moved, forms an angle of 45° with plane contact faces 15A, 15B and 16A, 16B respectively.

Measurement unit 13 comprises a plurality of light emitters 20A, 20B; 21A, 21B, which are disposed around the periphery of the hose line in a first plane, as shown in FIG. 2A. The axes of the adjacent light emitters each form an angle of 90°. Light detectors 22A, 22B, 22C, 22D are disposed in a second plane, which is different from the first plane, as shown in FIG. 2B. In the present exemplary embodiment, the measurement unit comprises four light detectors, which are disposed around the periphery of the hose line. The light emitters and light detectors are light-emitting diodes (LEDs).

In the measurement unit according to the present invention, there are assigned to at least one of light detectors 22A to 22D in each case two light emitters 20A, 20B and 21A, 21B respectively, which simultaneously emit light which the at least one light detector 22A to 22D receives. The two light emitters of a group of light emitters, for example light emitters 20A and 20B, lie opposite one another. Associated light detector 22A to 22D is disposed in a plane which forms an angle of 90° with the plane in which light emitters 20A, 20B are disposed.

The light yield is doubled with the measurement unit according to the present invention, since the light from, in each case, two light emitters is evaluated by the light detectors. Moreover, the influence of different hose thicknesses within the measuring channel on the measurement result is reduced, since the measurement takes place over different measurement sections.

Whereas clamping unit 12 is shown only in a very simplified schematic representation in FIGS. 2A and 2B, FIGS. 3A and 3B show particularly preferred embodiments of receiving elements 15, 16 of clamping unit 12 in a partially cut-away perspective representation. The parts corresponding to one another are provided with the same reference numbers.

Figure 3A:
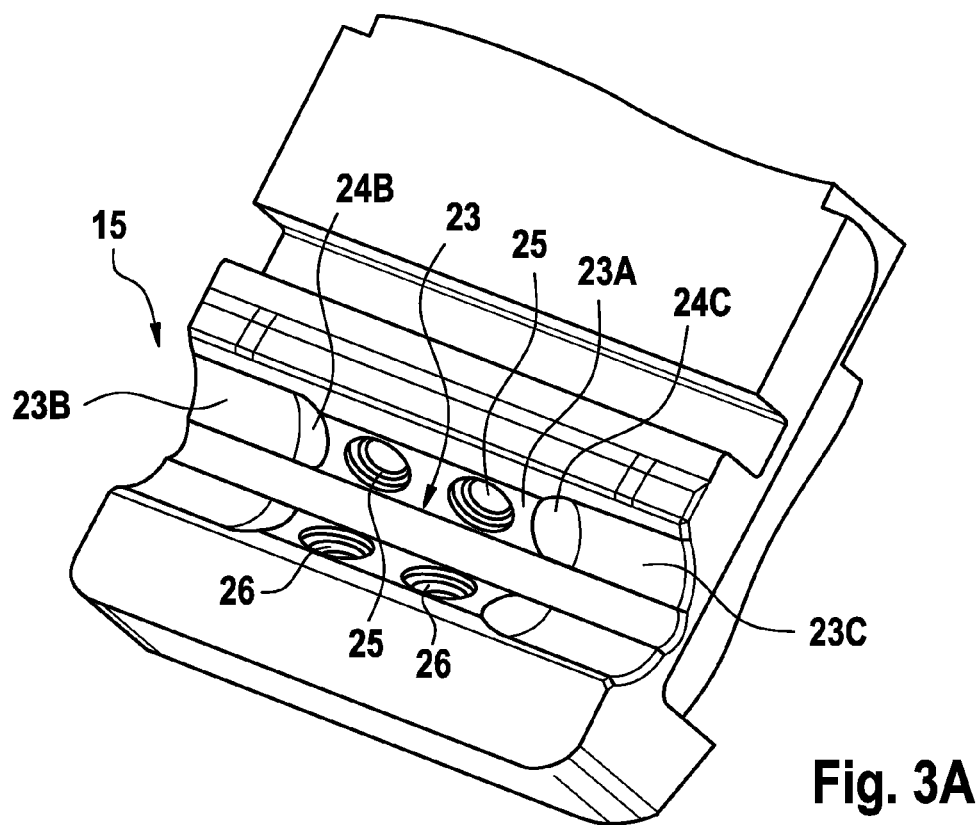
FIG. 3A shows the one receiving element of the clamping unit in a perspective representation according to an exemplary embodiment of the present invention.
Figure 3B:
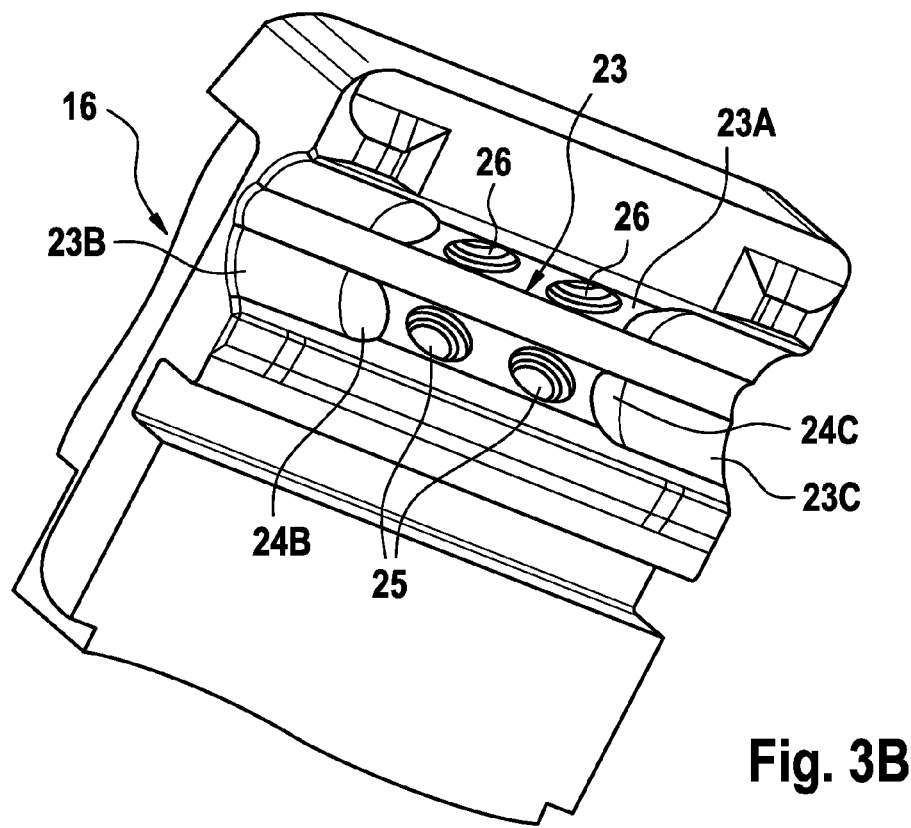
FIG. 3B shows the other receiving element of the clamping unit in a perspective representation according to an exemplary embodiment of the present invention.

The two receiving elements 15, 16 are again moved by an actuation mechanism which is driven by an electric motor, not represented, said actuation mechanism not however being represented in FIGS. 3A and 3B for the sake of better clarity. In this regard, reference is made to the schematic representation of FIGS. 2A and 2B.

In the closed position, the receiving elements form a measuring channel 23, which comprises an inner section 23A and two outer sections 23B, 23C, which are disposed on both sides of the inner section 23A. Within inner section 23A, the receiving channel has the square cross-section shown in FIGS. 2A and 2B, whereas in outer sections 23B and 23C the receiving channel has a circular cross-section which corresponds to the cross-section of inserted hose line 17.

Each receiving element 15, 16 comprises two plane contact faces standing at right angles to one another in the inner section 23A and in each case a semi-cylindrical contact face in outer sections 23B, 23C, which in the closed position of the clamping element complement one another to form the square and circular measuring channel.

Located between the semi-cylindrical contact faces of outer sections 23B, 23C and the two plane contact faces of inner section 23A of each receiving element 15, 16 is a transition section 24B, 24C, in which the semi-cylindrical contact faces are transformed continuously into the plane contact faces. As a result, the hose line is not kinked on the one hand and on the other hand the formation of turbulence is avoided when blood is flowing through the hose line.

Light emitters 20A, 20B, 21A, 21B and light detectors 22A to 22D are disposed inside the square measuring channel in inner sections 23A of receiving elements 15, 16. The plane contact faces of the receiving elements comprise corresponding light outlet and inlet openings 25, 26.

In order to detect hose line 17 in clamping unit 12, device 11 for determining the concentration of blood constituents comprises a monitoring unit 27, as shown in FIG. 1. Monitoring unit 27 comprises a unit 27A, represented only in outline, for measuring the motor current of electric motor 19 with which actuation mechanism 18 of clamping unit 12 is driven. Instead of the motor current, however, a variable correlating with the motor current, for example the motor power, can also be measured. Moreover, monitoring unit 27 comprises a unit 27B, again represented only in outline, for measuring the path on which receiving elements 15, 16 are moved from the opened position into the closed position. The measured values of units 27A, 27B for measuring the motor current and the path covered are evaluated by computing and evaluation unit 27C, which is a component part of monitoring unit 27 in the present example of embodiment. Computing and evaluation unit 27C of monitoring unit 27 is connected via a data line 28 to central control unit 10 of the extracorporeal blood treatment apparatus. It can however also be a component part of central control unit 10.

Figure 4A:
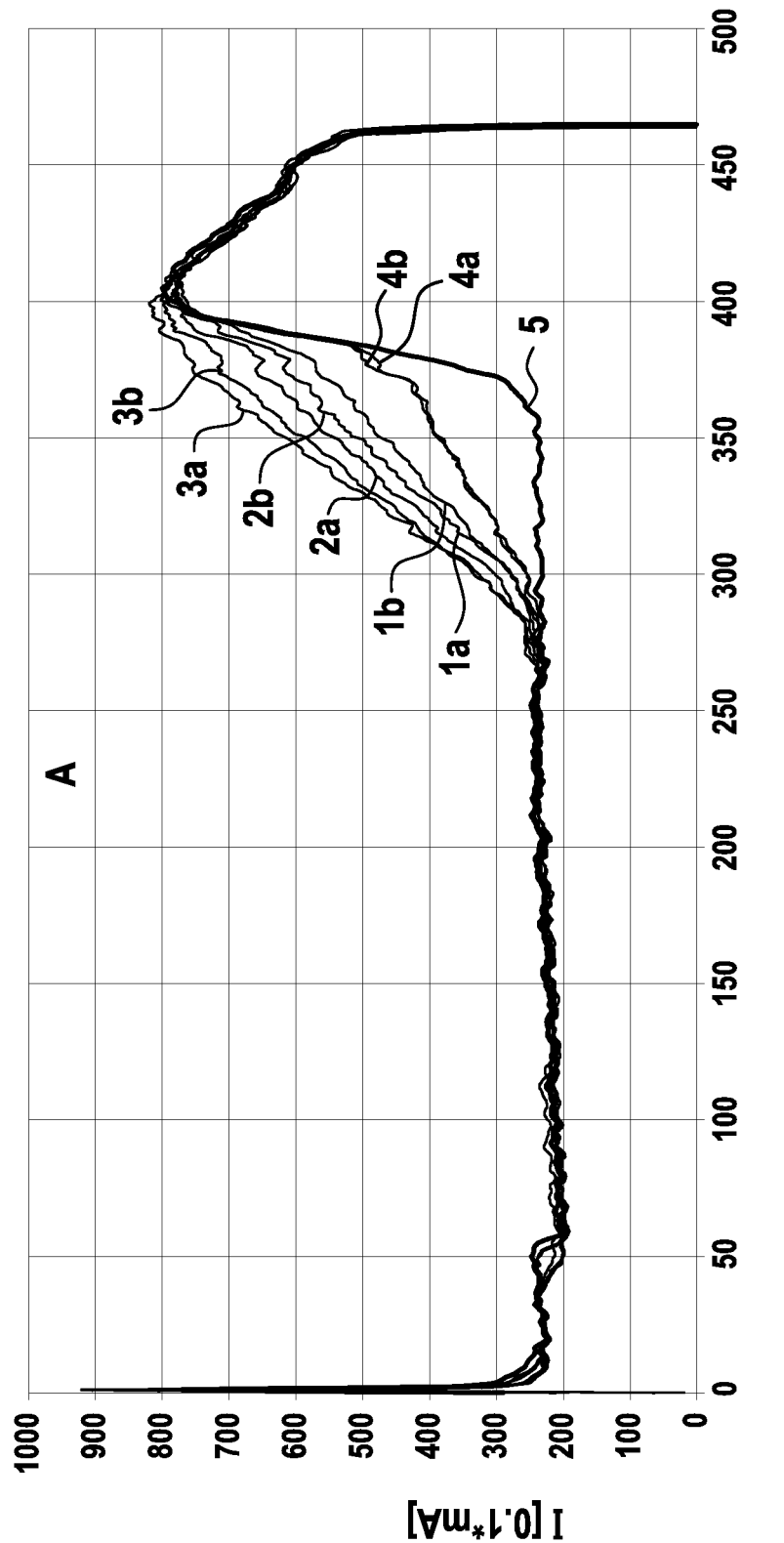
FIG. 4A shows the time-related characteristic of the motor current of the electric motor for the electromotive actuation of the clamping unit, said motor current being measured in a first clamping unit, according to an exemplary embodiment of the present invention.
Figure 4B:
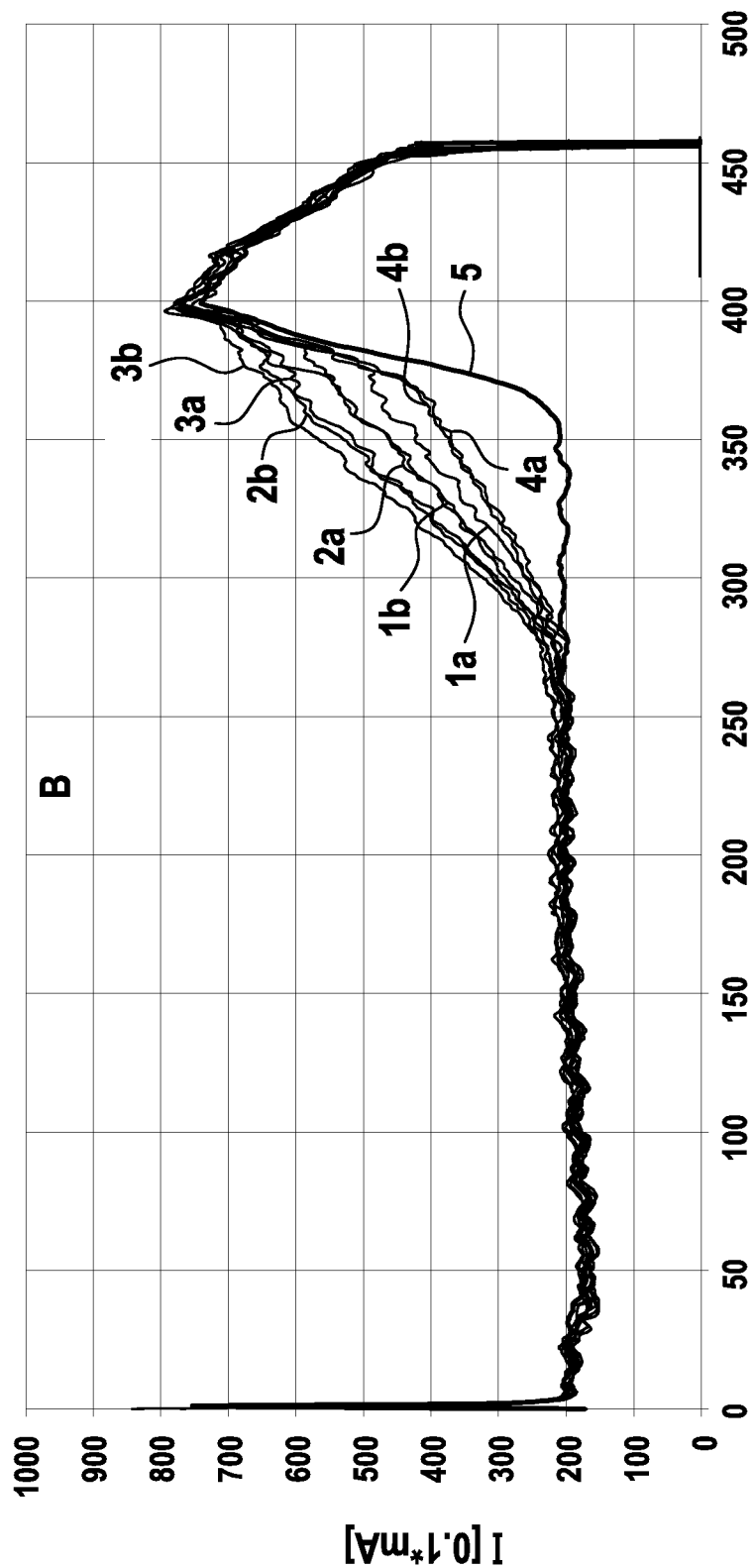
FIG. 4B shows the time-related characteristic of the motor current measured in a second clamping unit according to an exemplary embodiment of the present invention.
Figure 4C:
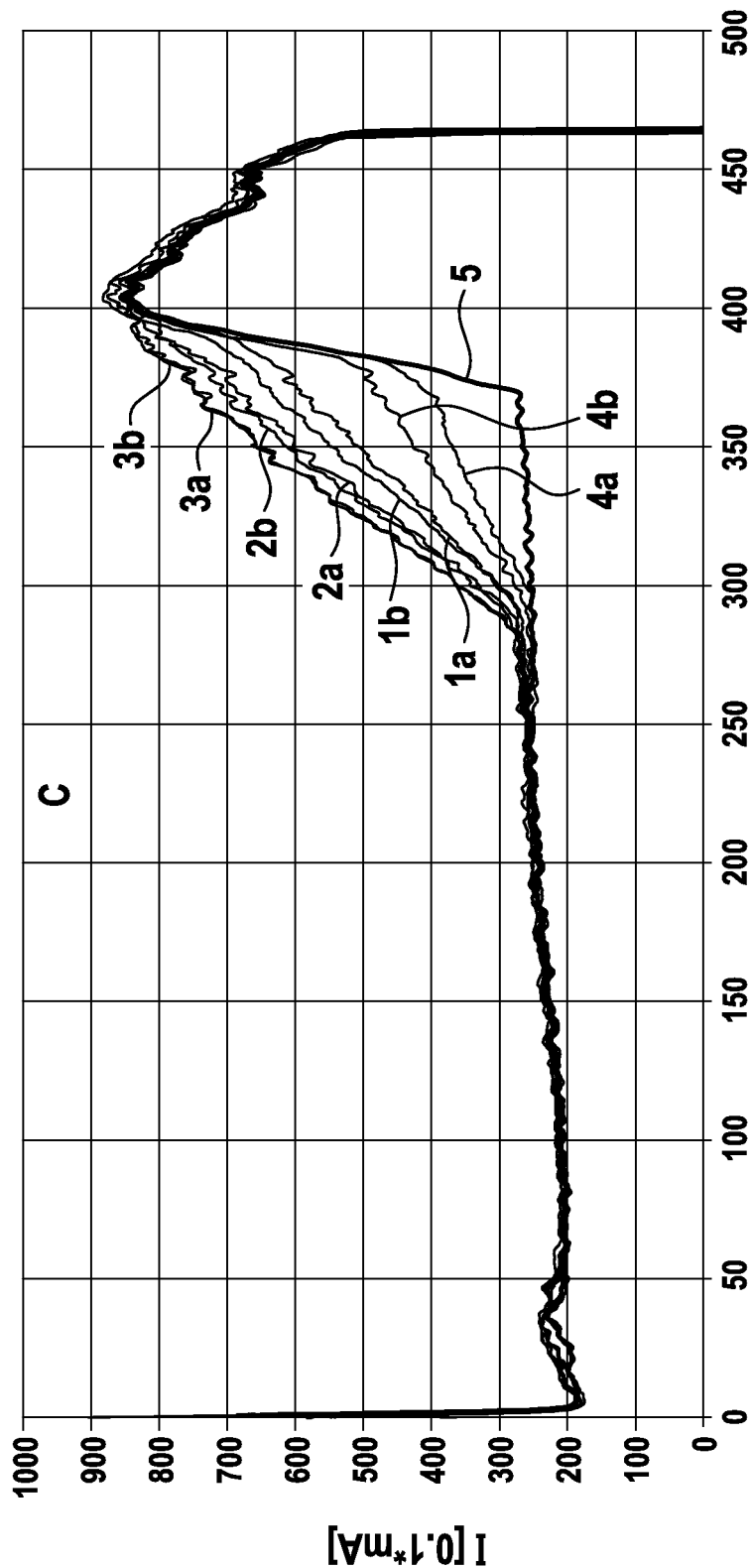
FIG. 4C shows the time-related characteristic of the motor current measured in a third clamping unit according to an exemplary embodiment of the present invention.

Computing and evaluation unit 27C of monitoring unit 27 calculates the integral of the measured motor current over a path which is covered by receiving elements 15, 16 during the closing of clamping unit 12. The calculated integral of the motor current is compared with a preset threshold value. If the threshold value is exceeded, computing and evaluation unit 27C of monitoring unit 27 ascertains that a hose line is inserted into clamping unit 12. Otherwise, the computing and evaluation unit ascertains that a hose line is not inserted. In both cases, the computing and evaluation unit generates a corresponding signal, which is received by the central control unit of the blood treatment apparatus. In detail, computing and evaluation unit 27C of monitoring unit 27 operates as follows:

The variation of the motor current is monitored over a specific path interval. In the present exemplary embodiment, the start of the path is N1=250 and the end of the path is N2=350, as shown in FIGS. 4A, 4B, and 4C. The path difference between measurement points I(n) and I(n+1) is $\Delta x(n)$.

The computing and evaluation unit calculates the integral for the preset path between N1 and N2 as follows, according to equation (1):

$$A = \sum_{N1}^{N2} [I(n) - I(N1)] \cdot \Delta x(n) \qquad \text{equation (1)}$$

FIGS. 4A, 4B and 4C show the measured motor current I [0.1×mA] of the electric motor for driving the actuation mechanism as a function of the path x covered by the receiving elements during the closing of the clamping unit. The path covered by the receiving elements can be detected by a device which generates a specific number of electrical pulses per revolution of the motor. The number of measured electrical pulses, which corresponds to the path covered, is plotted here on the x-axis.

FIGS. 4A to 4C show the measurement results for three different clamping units of differing design, which are denoted in the Figures as modules A, B and C. FIGS. 4A to 4C represent the variation of the motor current during the closing of the clamping unit for four different hose lines, which are either empty or filled with $H_2O$. The individual curves are designated as follows in FIGS. 4A to 4C:

5: clamping unit without hose
    1a: PVC hose (standard wall thickness) in clamping unit
    1b: PVC hose filled with $H_2O$ (standard wall thickness) in clamping unit
    2a: PVC hose (thin wall thickness) in clamping unit
    2b: PVC hose filled with $H_2O$ (thin wall thickness) in clamping unit
    3a: PVC hose (thick wall thickness) in clamping unit
    3b: PVC hose filled with $H_2O$ (thick wall thickness) in clamping unit
    4a: empty hose (different material) in clamping unit
    4b: hose filled with $H_2O$ (different material) in clamping unit For all the measurements with different hose lines and different clamping units, it emerges that, when the clamping unit is closed, the motor current increases earlier when a hose line is inserted than when no hose line is inserted. Moreover, it emerges that the increase in current when a hose line is inserted is sharper than when no hose line is inserted. The area under the curves when a hose line is inserted is therefore greater than when a hose line is not inserted.

Figure 5:
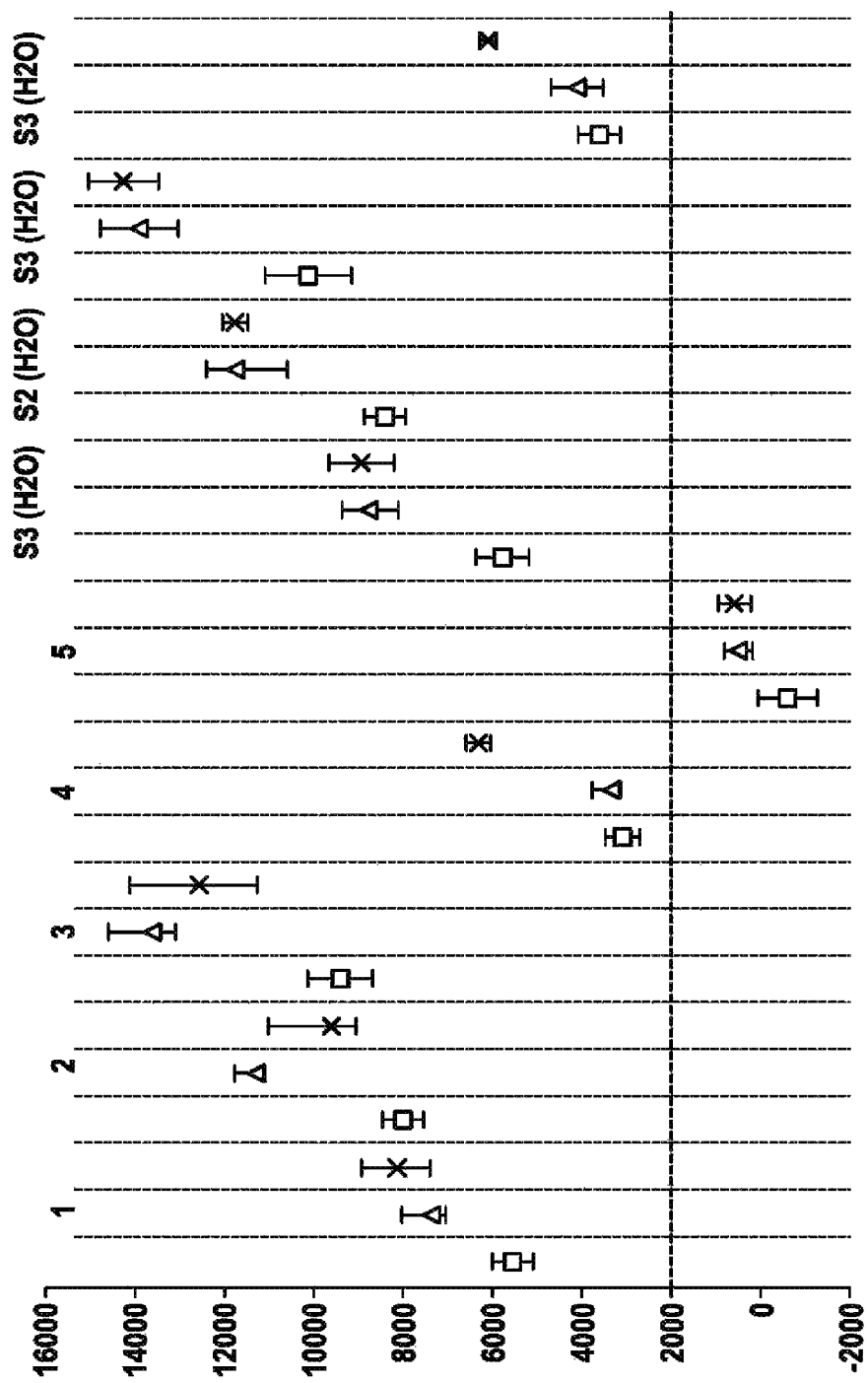
FIG. 5 shows an evaluation of the measurement results from FIGS. 4A to 4C, according to an exemplary embodiment of the present invention.

FIG. 5 shows the evaluation of the measurement results represented in FIGS. 4A to 4C. FIG. 5 represents the measurement results from FIG. 4A with a rectangle, those from FIG. 4B with a triangle and those from FIG. 4C with a cross. The integral was calculated according to equation (1) for the individual hose lines PVC hose (standard wall thickness) 1, PVC hose (thin wall thickness) 2, PVC hose (thick wall thickness) 3, hose (different material) 4, and no hose 5. For PVC hose (standard wall thickness) 1, the value of the integral in 0.01×mA×mm lies between 4500 and 9500 for all the measurements with the different clamping units both for the case where the hose is empty (1$a$) as well as for the case where the hose is filled with $H_2O$ (1$b$). For PVC hose (thin wall thickness) 2, the value of the integral for the measurements lies between 7500 and 12,500, whereas for PVC hose (thick wall thickness) 3, the value of the integral lies between 8500 and 15,000. For hose (different material) 4, the value of the integral is much lower between 2500 and 6500. It emerges that the value of the integral lies below 2000 when no hose 5 is inserted into the clamping unit.

In the present exemplary embodiment, 2000 is adopted as the preset threshold value for the value of the integral. For all the hoses, it is thus possible with different clamping units to distinguish reliably between the case where a hose is inserted into the clamping unit and the case where a hose is not inserted into the clamping unit. If the hose (different material) 4 is not used, the preset threshold value can be higher. A threshold value of 3000 is fixed in the present exemplary embodiment.

Blood hoses made of PVC or PUR or other materials can be used for the measurement of the blood volume. In practice, therefore, there is not only the problem of detecting a blood hose in the clamping unit of the device for determining the concentration of a blood constituent, but also of identifying the type of blood hose inserted into the clamping unit.

It has been shown in practice that the material from which the blood hose is made can have an influence on the accuracy of the measurement of the concentration of a blood constituent. The identification of the blood hose therefore also allows conclusions to be drawn as to the accuracy of the measurement. Thus, it is possible to give an acoustic and/or optical indication of the measurement accuracy. The measurement can also be corrected or even prevented depending on the blood hose used.

A computing and evaluation unit of the monitoring unit is described below, which apart from detecting the blood hose also permits the identification of the type of blood hose.

A high measurement accuracy is achieved in practice with a blood hose made of PUR, which is characterised by a low tolerance of the wall thickness. Compared to a hose made of PVC, a hose made of PUR is characterised by a greater hardness and a higher elasticity. The PUR hose thus exerts a greater restoring force on the receiving elements of the receiving unit.

Tests have shown that a distinction between a blood hose made PUR and PVC can be made with a particularly high degree of reliability with the method according to the present invention and the device according to the present invention when the blood hose is pre-compressed, before the measurement, for a preset period between the receiving elements.

The device according to the present invention and the method according to the present invention therefore make provision such that, after the insertion of the hose line into clamping unit 12, actuation mechanism 18 is operated in order to close receiving elements 15, 16, in which the receiving elements are closed until such time as a preset pressing force is exerted on the hose line, and after a preset time interval the receiving elements are opened again. In order to perform the actual measurement, the receiving elements are then closed again. This process can be controlled fully automatically by monitoring unit 27.

An exemplary embodiment is described below, in which a calibration is provided to increase the measurement accuracy.

The ratio of current and torque is generally described by the following equation:

$$i_n(m) = k_n \cdot m$$

where m is the torque, k is a constant and n is a designation (number) of the clamping unit used in the measurement.

It has been shown that the individual clamping units of the same design may differ from one another in the closing behavior on account of tolerances of the actuation mechanism.

Figure 6:
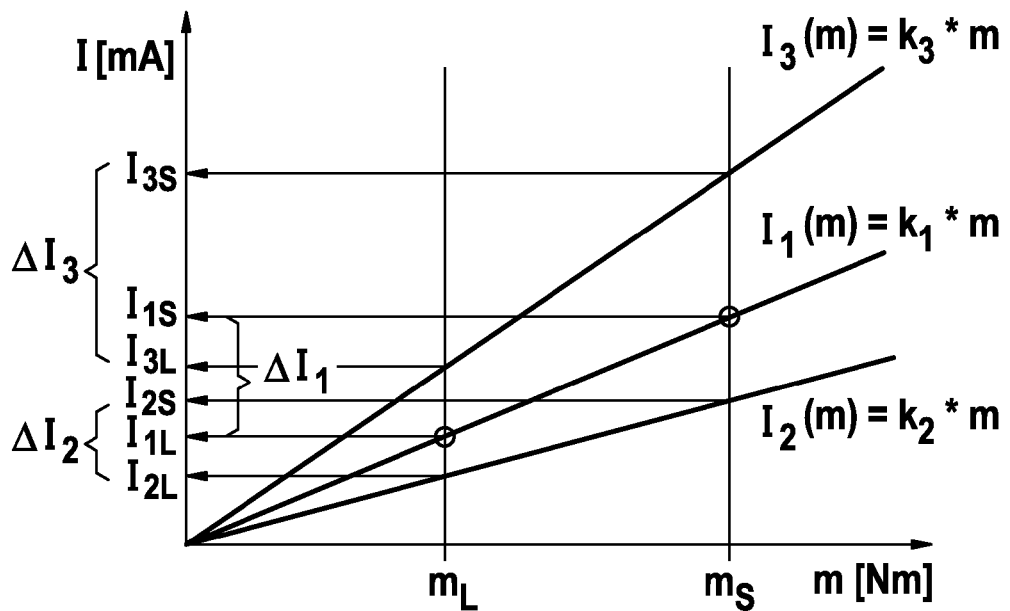
FIG. 6 shows the motor current as a function of the torque, according to an exemplary embodiment of the present invention.

FIG. 6 shows motor current I [mA], which is measured by the unit 27A for measuring the motor current, as a function of torque m [Nm] which is developed by electric motor 19. The ratio of current and torque $I_1(m)$, $I_2(m)$, $I_3(m)$ is represented for three different clamping units 15. The circle at $m_L$ shows the operating point of the no-load measurement, at which the hose is not inserted into the clamping unit, and the circle at ms shows the operating point of the hose compression, at which the hose is inserted into the clamping unit. With an increasing k-value, current difference $\Delta I_n$ between no-load measurement $\Delta I_{nL}$ and hose compression $\Delta I_{nS}$ increases ($\Delta I_3 > \Delta I_1 > \Delta I_2$). It follows from this that, to eliminate the influence of the tolerances of the clamping unit on the measurement, it is not sufficient to take account of an offset ascertained only with a no-load measurement. A 1-point calibration with a calibration factor k is therefore carried out.

Monitoring unit 27 is designed in such a way that a measurement is carried out with the following calibration. All the computing operations can be carried out in a microprocessor, not represented, which is part of computing and evaluation unit 27C of monitoring unit 27.

For this purpose, the microprocessor of computing and evaluation unit 27C is programmed for the performance of the following computing operations.

Receiving elements 15, 16 of clamping unit 27 are first opened by an electric motor, insofar as they are not already open, in order to be able to carry out a no-load measurement in which a hose line is not inserted. Receiving elements 15, 16 are then closed by an electric motor in order to perform the no-load measurement, in which the motor current $I_L(x)$ is measured with the unit 27A for measuring the motor current. The measurement for ascertaining the no-load current does not need to be carried out before each blood treatment. It is sufficient for the measurement to be carried out at preset time intervals, for example at an interval of one month. An inherent system influence is eliminated with the no-load measurement.

In order to increase the reliability of the calibration, provision can be made to repeat the no-load measurement several times. The characteristic of the motor current is thereby integrated and the integral values are averaged over the number of measurements.

Receiving elements 15, 16 of clamping unit 12 are then opened up again so that the hose line can be inserted. A preliminary compression of the hose line preferably takes place before the actual measurement with the hose compression.

For the preliminary compression of the hose line, receiving elements 15, 16 are closed by a preset path x with the hose line inserted, in order to exert a preset pressing force on the hose line, which is dependent on the material as well as the diameter and wall thickness of the hose line. The preliminary compression of the hose line preferably takes place during the filling or rinsing procedure of the blood treatment apparatus. In this phase, the hose line is filled with a fluid which has a preset temperature. During the filling or rinsing procedure, the temperature of the rinsing fluid is for example 36°, the flow rate of the fluid being for example 400 ml/min. The duration of the preliminary compression can amount to 3 min. These values have proved in practice to be particularly advantageous for the preliminary compression.

After the preliminary compression, receiving elements 15, 16 are again opened and closed for the performance of the actual measurement, in order to measure motor current $I_S(x)$ with hose compression as a function of path x.

Motor current $I(x)$ is then calculated according to the following equation (2):

$$I(x) = I_S(x) - I_L(x) - I_0 \quad \text{equation (2)}$$

The integral is now calculated according to the following equation (3):

$$A = k \cdot \int_{x_1}^{x_2} [I_S(x) - I_L(x) - I_0] dx \quad \text{equation (3)}$$

where k is a calibration factor, $x_1$ and $x_2$ meet the condition $I(x_1) \geq 0$ and $I(x_2) \geq 0$ and $I_0$ is a preset current, for example 5 mA.

The following calibration is carried out to determine calibration factor k. For the calibration, a reference value is calculated for integral $A_{Ref}$ in a plurality of measurements with a plurality of clamping units of the same design, the mean value of ascertained integrals $A_n$ being calculated for the calculation of the reference value. In addition, integral $A_0$ is calculated for clamping unit 12 to be calibrated.

Calibration factor k is then calculated according to the following equation (4):

$$k = \frac{A_{Ref}}{A_o} \quad \text{Equation (4)}$$

Integral A calculated according to equation (3) is compared with a preset threshold value in computing and evaluation unit 27C. For this purpose, computing and evaluation unit 27C comprises a comparison unit, not represented.

If calculated integral A is greater than the preset threshold value, it is established that a hose line of a first type is inserted, the hose line being for example a PUR hose. If, on the other hand, the calculated integral is less than the preset threshold value, it is established that a hose line of a second type is inserted, the hose line being for example a PVC hose.

A preferred embodiment makes provision such that a statement cannot be made about the material properties when calculated integral A lies in a value range which lies between a preset first threshold value, for example for a PUR hose, and a preset second threshold value, for example for a PVC hose, the first threshold value for the PUR hose being greater than the second threshold value for the PVC hose. A PUR hose is therefore identified when the integral is greater than the upper first threshold value, whereas a PVC hose is identified when the integral is less than the lower second threshold value.

When computing and evaluation unit 27C has established that the hose line is a PUR hose or a PVC hose, a first or second control signal is generated. The type of the hose line used can for example be displayed on a display unit, not represented, of monitoring unit 27. It is also possible to display on the display unit when integral A is less than the upper first threshold value and greater than the second lower threshold value, i.e., lies in the aforementioned value range, so that a determination of the type of the hose line used is not possible with a high degree of reliability.

It has been shown in tests that the hose line type can be reliably identified by comparing the integral with an upper and lower threshold value. Alternatively, maximum value $I_{max}$ of the measured current can also be determined to identify a hose line type, the maximum value of current $I_{max}$ being compared with a threshold value. If maximum value $I_{max}$ of the measured current lies above the threshold value, it is concluded that it is the one hose line type, for example the PUR hose, and if maximum value $I_{max}$ of the measured current lies below the threshold value, it is concluded that it is the other hose line type, for example the PVC hose. The edge steepness of the current increase can also be compared with a threshold value in order to identify the hose line type. These operations can again be carried out by the comparison unit.

It is also possible to carry out a determination of the hose line on the basis of a combination of two or three of the aforementioned variables in order to increase further the reliability. The monitoring unit then concludes that there is a specific hose line only when it is concluded that there is a specific hose line type in an evaluation on the basis of two variables or on the basis of all the variables.

In the first alternative embodiment, the evaluation unit makes provision to conclude that there is a PUR hose if the maximum value of current $I_{max}$ is greater than a preset threshold value, whilst it is concluded that there is a PVC hose if the maximum value of current $I_{max}$ is less than a preset threshold value.

In the second alternative embodiment, the evaluation unit makes provision to conclude that there is a PUR hose if the edge steepness of the current increase, i.e., the derivative of the function in the region of the edge of the current increase, is greater than a preset threshold value, whilst it is concluded that there is a PVC hose if the edge steepness of the current increase is less than a preset threshold value.

Figure 7:
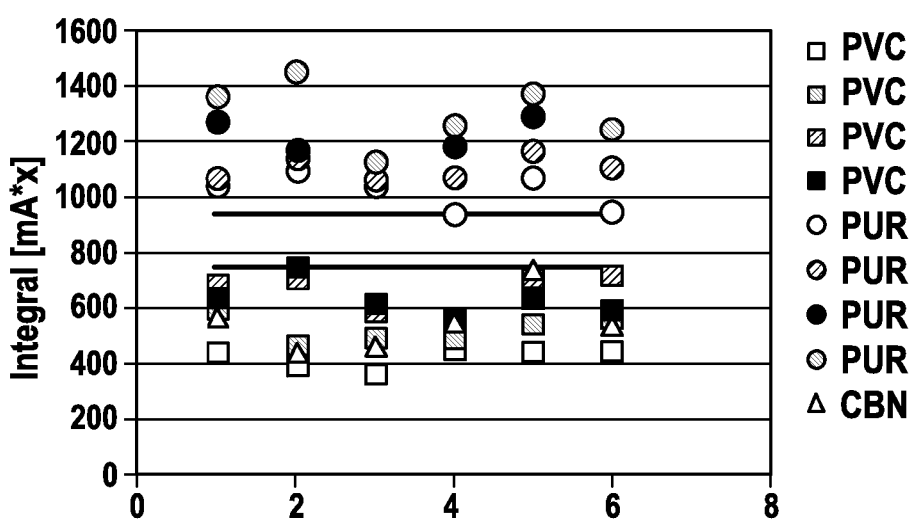
FIG. 7 shows the measurement results for six clamping units of identical design and different hose lines, according to an exemplary embodiment of the present invention.
Figure 8A:
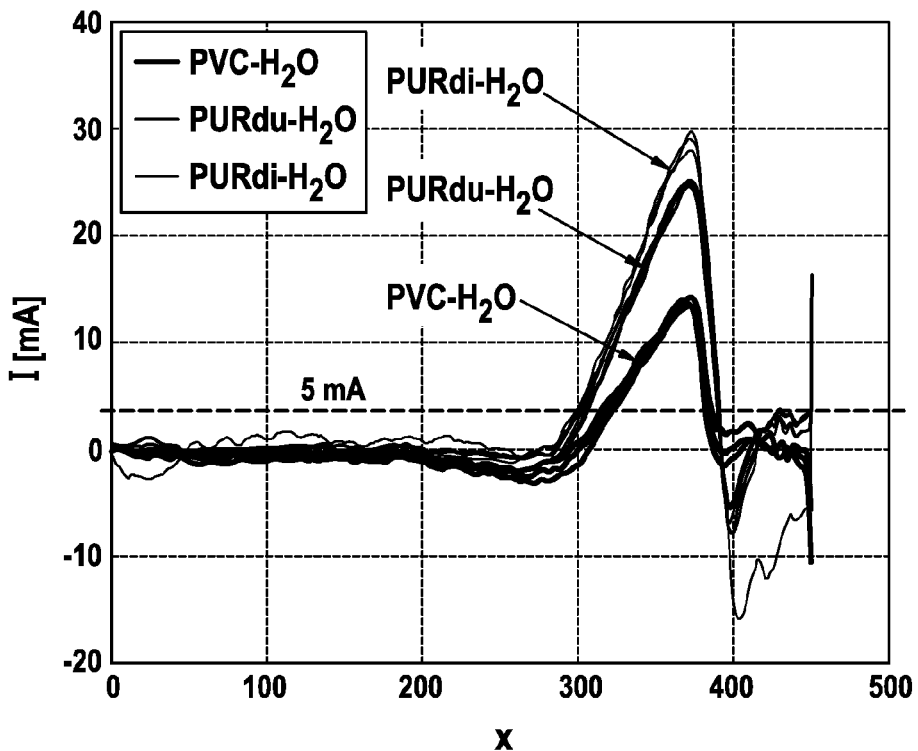
FIGS. 8A to 8D show motor current I as a function of motor path x for the clamping units of the same design and the different hose types, according to an exemplary embodiment of the present invention.
Figure 8B:
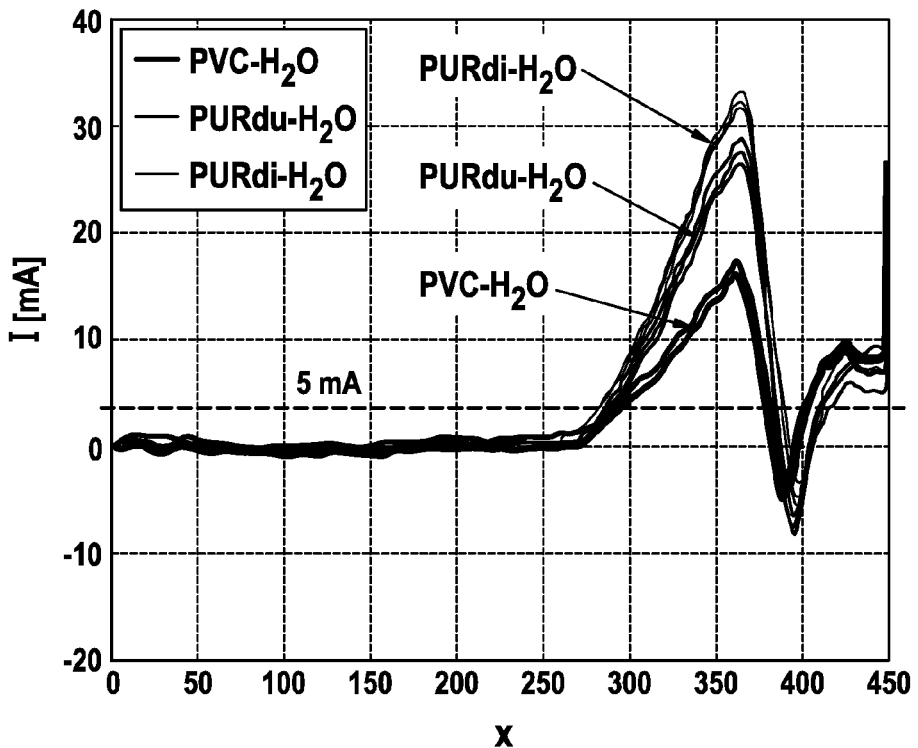
Figure 8C:
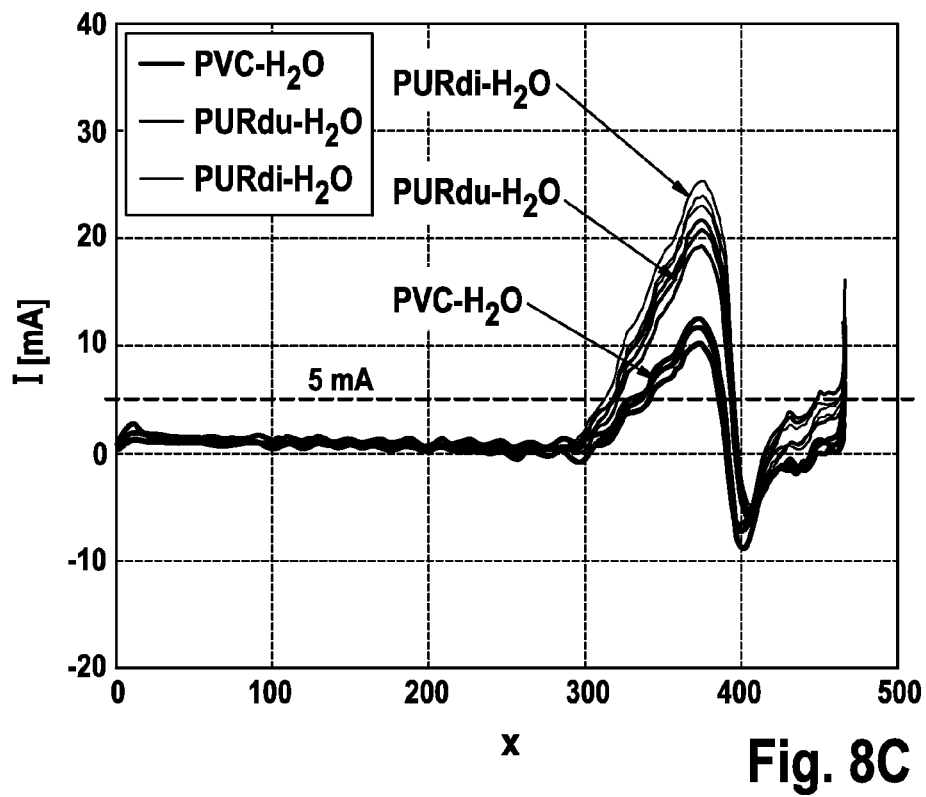
Figure 8D:
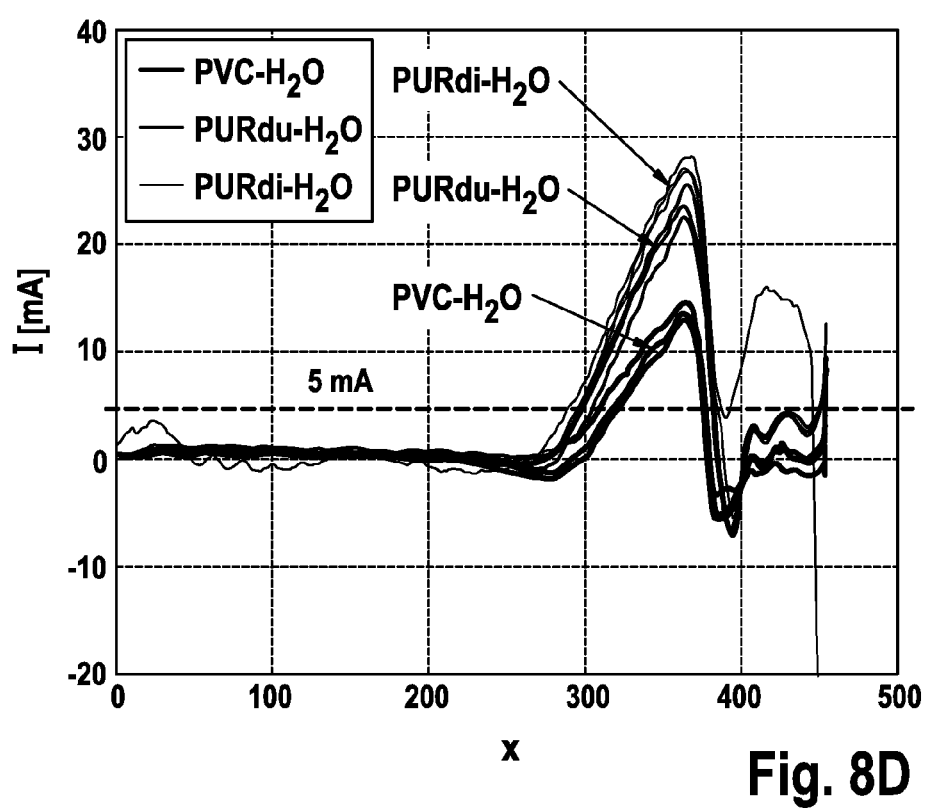

FIG. 7 shows the measurement results for six clamping units 1 to 6 of the same design and four different PVC hoses and four different PUR hoses as well as a further hose CBN of a different material, in which the PVC hoses in FIG. 7 are indicated by rectangles, the PUR hoses by circles, and the CBN hose by triangles. The value range in which a reliable identification of the hose type is not guaranteed lies between the upper threshold value, which is indicated in FIG. 7 by the upper horizontal line (threshold value (PUR)), and the lower threshold value, which is indicated by the lower line (threshold value (PVC)).

The reliability margin between the upper and lower line is calculated from the quotient of the difference between the upper threshold value (PUR) and the lower threshold value (PVC) and the mean value of the threshold values.

The measurement method described above was tested with four clamping units A, B, C, D, use being made of a thin PUR hose with a small wall thickness, a thick PUR hose with a large wall thickness and a standard hose of PVC. The hose was filled with water for the test, the water being at a temperature of 36.6°. The water was pumped through the hoses.

FIGS. 8A to 8D show motor current I [mA] smoothed out over 10 points as a function of motor path x for individual clamping units A, B, C, D, the thin PUR hose with a small wall thickness being denoted by PURdu, the thick PUR hose with a large wall thickness by PURdi and the standard PVC hose by PVC. The preselected constant current $I_0$ is 5 mA.

FIG. 9 shows a table, in which integral A, maximum current $I_{max}$ and the edge gradient dI/dr for the individual clamping units A, B, C, D and the different host types PVC and PUR are entered. The reliability margin is denoted by $\Delta$ in the table.

It can be seen that the value ranges of the different evaluation methods on the basis of integral A, maximum current $I_{max}$ and the edge gradient dI/dx do not intersect. Consequently, the individual types of hose can be unequivocally identified. The highest degree of reliability in identification of the hose type, however, is seen with the evaluation on the basis of the integral.

What is claimed is:

1. A device for determining a concentration of a constituent of blood in a hose line of an extracorporeal blood circuit of an extracorporeal blood treatment apparatus, comprising:
a clamping unit comprising a first receiving element and a second receiving element configured to clamp the hose line such that the hose line clamped between the first and second receiving elements has a square cross-section;
a measurement unit configured to couple electromagnetic radiation through the hose line into the blood and measure the electromagnetic radiation emerging through the hose line from the blood; and
a computing and evaluation unit configured to determine the concentration of a constituent of blood, said computing and evaluation unit cooperating with the measurement unit;
wherein the clamping unit comprises an actuation mechanism configured to apply a clamping force such that the first and second receiving elements are moved towards one another from a first position releasing the hose line into a second position clamping the hose line, the actuation mechanism comprising an electric motor for driving the actuation mechanism.

2. The device according to claim 1, further comprising:
a monitoring unit configured to detect a hose line inserted into the receiving elements.

3. The device according to claim 2, wherein the monitoring unit comprises a unit for measuring one of (a) a motor current of the electric motor for driving the actuation mechanism of the clamping unit and (b) a variable correlating with the motor current, and a computing and evaluation unit configured to detect a hose line inserted into the receiving elements on a basis of a change in one of (a) the measured motor current and (b) the measured variable correlating with the motor current.

4. The device according to claim 3, wherein the monitoring unit is configured to correct with a correction value the motor current measured by the unit for measuring the motor current, the correction value being obtained in a calibration measurement when the hose line is not inserted into the clamping unit.

5. The device according to claim 3, wherein the monitoring unit comprises a unit for measuring a path covered by the receiving elements, and the computing and evaluation unit of the monitoring unit is configured to evaluate the motor current as a function of the path covered by the receiving elements.

6. The device according to claim 5, wherein the computing and evaluation unit of the monitoring unit is configured to compare with a preset threshold value at least one of (a) an integral of the motor current and (b) a maximum value of the motor current over a preset path covered by the receiving elements, it being concluded that one of (i) a hose line is inserted into the receiving elements when the threshold value is exceeded, and (ii) a specific first hose line is inserted into the receiving elements when the threshold value is exceeded and a specific second hose line is inserted into the receiving elements when the threshold value is fallen below, the first and second hose line being different hose lines.

7. The device according to claim 1, wherein the first receiving element comprises two plane contact faces at right angles to one another, and the second receiving element comprises two plane contact faces at right angles to one another, wherein the first and second receiving elements can be moved towards one another on an axis that encloses an angle of 45° with the plane contact faces of the first and second receiving elements.

8. The device according to claim 7, wherein the first receiving element comprises semi-cylindrical contact faces on both sides of the plane contact faces of the first receiving element, and the second receiving element comprises semi-cylindrical contact faces on both sides of the plane contact faces of the second receiving element.

9. The device according to claim 8, wherein the first receiving element comprises a transition section on both sides of the plane contact faces configured to transform continuously the plane contact faces into the semi-cylindrical contact faces.

10. The device according to claim 1, wherein the measurement unit comprises light emitters and light detectors disposed in the first and second receiving elements.

11. The device according to claim 10, wherein plane contact faces of the receiving elements comprise light outlet and light inlet openings assigned to the light emitters and the light detectors.

12. The device according to claim 10, wherein at least one group of two light emitters is assigned to at least one light detector.

13. The device according to claim 12, wherein the two light emitters of the at least one group of light emitters are disposed on sides lying opposite one another.

14. A method for detecting a hose line of an extracorporeal blood circuit of an extracorporeal blood treatment apparatus, in a clamping unit of a device for determining a concentration of a blood constituent, the clamping unit comprising a first receiving element and a second receiving element for clamping the hose line, and an actuation mechanism comprising an electric motor for driving the actuation mechanism, the method comprising:
applying a clamping force by the actuation mechanism such that the first and second receiving elements are moved out of a first position releasing the hose line into a second position clamping the hose line;
measuring one of (a) a motor current and (b) a variable correlating with the motor current, of the electric motor for driving the actuation mechanism of the clamping unit; and
detecting the hose line inserted into the receiving elements on a basis of a change in one of (a) the measured motor current and (b) the measured variable correlating with the motor current.

15. The method according to claim 14, further comprising:
correcting the measured motor current with a correction value that is obtained in a calibration measurement when the hose line is not inserted into the clamping unit.

16. The device according to claim 14, further comprising:
measuring a path covered by the receiving elements; and
evaluating the motor current as a function of the path covered by the receiving elements.

17. The method according to claim 16, further comprising:
comparing with a preset threshold value at least one of (a) an integral of the motor current and (b) a maximum value of the motor current over a preset path covered by the receiving elements; and
concluding that one of (a) a hose line is inserted into the receiving elements when the threshold value is exceeded, and (b) a specific first hose line is inserted into the receiving elements when the threshold value is exceeded and a specific second hose line is inserted into the receiving elements when the threshold value is fallen below, the first and second hose lines being different hose lines.

* * * * *